(12) United States Patent
Soto-Thompson et al.

(10) Patent No.: US 8,289,378 B2
(45) Date of Patent: Oct. 16, 2012

(54) HIGH RESOLUTION DIGITAL VIDEO COLPOSCOPE WITH BUILT-IN POLARIZED LED ILLUMINATION AND COMPUTERIZED CLINICAL DATA MANAGEMENT SYSTEM

(75) Inventors: Marcelo Esteban Soto-Thompson, Honolulu, HI (US); Andrew Beaumont Whitesell, Honolulu, HI (US); Ulf Peter Gustafsson, Honolulu, HI (US)

(73) Assignee: STI Medical Systems, LLC, La Jolla, CA (US)

( * ) Notice: Subject to any disclaimer, the term of this patent is extended or adjusted under 35 U.S.C. 154(b) by 947 days.

(21) Appl. No.: 12/291,890

(22) Filed: Nov. 14, 2008

(65) Prior Publication Data

US 2010/0026785 A1 Feb. 4, 2010

Related U.S. Application Data

(60) Provisional application No. 61/137,684, filed on Aug. 1, 2008.

(51) Int. Cl.
*H04N 13/02* (2006.01)
(52) U.S. Cl. ................ 348/47; 348/57; 348/58
(58) Field of Classification Search ......... 348/47
See application file for complete search history.

(56) References Cited

U.S. PATENT DOCUMENTS

| | | | |
|---|---|---|---|
| 5,929,443 A | 7/1999 | Alfano et al. | |
| 6,766,184 B2 | 7/2004 | Utzinger et al. | |
| 2006/0184040 A1* | 8/2006 | Keller et al. | 600/476 |
| 2006/0215406 A1* | 9/2006 | Thrailkill | 362/252 |

OTHER PUBLICATIONS

D. G. Ferris, et al., "Modern Colposcopy—Textbook and Atlas," pp. 250-662, American Society for Colposcopy and Cervical Pathology Kendall/Hunt Publishing Co., Dubuque, Iowa.
B.S. Apgar et al., "Colposcopy: Principles and Practice," pp. 115-132, W.B. Saunders Company, Philadelphia, PA 2002.
K. T. Schomacker et al., Novel optical detection system for in vivo identification and localization of cervical intra-epithelial neoplasia, J. Biomed Optics 11(3), pp. 034009-1 to 034009-02, 2006.
J.E. Kendrick et al., "LUMA™ Cervical Imaging System," Expert Rev. Med. Devices 4(2), pp. 121-129, 2007.
E. Hecht., "Optics," pp. 270-332, Addison-Wesley, 2nd edition 1987.
Welch Allyn, "Video Colposcope," Directions for Use, 2007.
S. Nakappan et al., "Methodology of real time quality control for the multispectral digital colposcope," Gynecologic Oncology 107, S21-S222, 2008.
Acgih, "Electromagnetic Radiation and Fields," pp. 13-43, 2007, Cincinati, OH.

* cited by examiner

*Primary Examiner* — Tonia L Dollinger
*Assistant Examiner* — Adam Cooney
(74) *Attorney, Agent, or Firm* — Martin E. Hsia (57) ABSTRACT

This invention uses LEDs and cross-polarization to produce bright, high-resolution digital images, both with and without glint (which adversely affects the clarity of standard colposcopic images), as well as streaming video at lower resolution. The invention allows for deeper layers of the tissue to be more efficiently visualized at multiple magnifications, thereby enhancing the invention's diagnostic capabilities, and it includes a focusing subsystem and a computerized data management system to archive and annotate still image data.

9 Claims, 9 Drawing Sheets

HIGH RESOLUTION DIGITAL VIDEO COLPOSCOPE WITH BUILT-IN POLARIZED LED ILLUMINATION AND COMPUTERIZED CLINICAL DATA MANAGEMENT SYSTEM

This application claims priority to U.S. provisional patent application No. 61/137,684 for "CervicalMD C30 Imaging Subsystem", filed on Aug. 1, 2008.

TECHNICAL FIELD

This invention relates to medical imaging and, more specifically, to a device and process that suppresses specular reflection (glint) through cross-polarization, producing bright cross-polarized and parallel-polarized images at multiple magnifications in real-time, thereby enhancing the visualization of diagnostically relevant features within a subject (such as organs or tissue). The device also preferably includes a focusing subsystem, and a computerized data management system for archival purposes and for the annotation of digital data.

BACKGROUND ART

Although this invention is being disclosed in connection with cervical cancer, it is applicable to many other areas of medicine. Uterine cervical cancer is the second most common cancer in women worldwide, with nearly 500,000 new cases and over 270,000 deaths annually (IARC, "Globocan 2002 database," International agency for research in cancer, 2002, incorporated herein by reference). Because invasive disease is preceded by pre-malignant Cervical Intraepithelial Neoplasia (CIN), if detected early and treated adequately, cervical cancer can be universally prevented (D. G. Ferris, J. T. Cox, D. M. O'Connor, V. C. Wright, and J. Foerster, *Modern Colposcopy. Textbook and Atlas*, pp. 1-699, American Society for Colposcopy and Cervical Pathology, 2004, incorporated herein by reference). Colposcopy is the primary diagnostic method in the United States to detect CIN and cancer following an abnormal cytological screen (Papanicolaou smear or pap smear). The purpose of a colposcopic examination is to identify and rank the severity of lesions, so that biopsies representing the highest-grade abnormality can be taken, if necessary. The biopsies are then microscopically evaluated by a pathologist based on the morphology of the tissue.

For the colposcopic exam, an optical colposcope is typically used, and has been used for such purposes for almost 80 years. A colposcope is a binocular microscope with a built in white light source and objective lens attached to a support mechanism (B. S. Apgar, Brotzman, G. L. and Spitzer, M., Colposcopy: Principles and Practice, W.B. Saunders Company: Philadelphia, 2002, incorporated herein by reference). At low levels of magnification, (comparable to a circular field of view of approximately 50 to 100 mm) the entire vagina and cervix can be visualized and this setting is typically used to obtain a general impression of the surface structure and architecture. Medium magnifications (comparable to a circular field of view of approximately 15-30 mm) and high magnifications (comparable to a circular field of view of approximately 5-15 mm) are utilized for detailed analysis of the vagina and the cervix. These higher magnifications are often necessary to detect and identify certain vascular patterns indicative of the presence of more advanced pre-cancerous or cancerous lesions. During the colposcopic exam, acetic acid and iodine solutions are usually applied to the surface of the cervix to improve the visualization of abnormal areas. In addition, different colored filters are often used to accentuate blood vessel patterns that cannot be easily seen by using regular white light.

Although the standard colposcopic exam and regular screening have led to dramatic decreases in the overall incidence of cervical cancer, new technologies can further enhance the sensitivity and specificity of currently accepted colposcopic practices. Digital imaging is one such technology that can revolutionize medical imaging and enables sophisticated computer programs to assist the physician with CAD (Computer-Aided-Detection or Computer-Aided-Diagnosis). The combination of digital imaging and CAD could have a direct impact on improving women's health, and decrease the associated cost, by automatically identifying CIN in real-time with high sensitivity and specificity. This would mean fewer false-positive biopsies, or ultimately, elimination of biopsies. A CAD system operating as an adjunct to colposcopy could minimize the high variability among colposcopists and enable consistent, higher standards for accuracy. A product realization where a CAD system is incorporated into a low-cost device, creating in effect a machine expert colposcopist, would have the potential of increasing the availability and cost-effectiveness of screening in developing countries.

Digital imaging provides a means for implementing a computerized clinical data management system. This data management system could provide management, display, and annotations of the acquired digital data, as well as automation of the workflow associated with colposcopy. The system could simplify the administration of patient data and history, allow the use of electronic patient data records, and interface and integrate with standard systems for handling, storing, printing and transmitting information in medical imaging, such as DICOM (Digital Imaging and Communication in Medicine). DICOM is a standard for handling, storing, printing, and transmitting information in medical imaging. It includes a file format definition and a network communications protocol. The communication protocol is an application protocol that uses TCP/IP (the standard internet protocol) to communicate between systems. DICOM files can be exchanged between two entities that are capable of receiving image and patient data in DICOM format. Digital imaging alone is also a pre-requisite for telemedicine applications, further increasing the availability of screening and detection in rural areas and developing countries.

In order to reliably assess colposcopic features, the imagery upon which a CAD system operates must be of high visual quality. One factor contributing to poor cervical imagery is specular reflection (glint), which is perfect, mirror-like reflection of light from a surface, in which light from a single incoming direction (i.e., a ray) is reflected into a single outgoing direction. Glint is undesirable because it effectively eliminates color information in an image, and also results in the introduction of artifacts (misrepresentations of tissue structures) in the image. Glint eliminates color information because its mirror-like reflection shows the color of the light source, and not of the underlying tissue, much as a mirror shows the color of a reflected light, and not the color of the mirror itself. Because this color information may be important in detecting cancer precursors, reducing the amount of glint in an image is helpful in producing high-quality images for diagnostic purposes. However, it is not always desirable to eliminate all the glint from an image because an image of a tissue or organ that contains glint may look more natural and three-dimensional. In addition, colposcopists analyze the glint patterns on the cervix to assess the surface contour of lesions, an important feature used to evaluate lesion severity.

The prior art describes a number of ways to reduce the influence of or eliminate glint. Physicians using optical colposcopes can change their field-of-view and/or the lightning conditions to either move the glint to different parts of the cervix and maintain the region of interest glint-free, or to a large extent eliminate the glint completely. Another method involves using multiple light sources directed at different angles towards an object (see for example K. T. Schomacker, T. M. Meese, C. Jiang, C. C. Abele, K. Dickson, S. T. Sum, and R. F. Flewelling, Novel optical detection system for in vivo identification and localization of cervical intra-epithelial neoplasia, J. Biomed Optics 11(3), 034009-1-12, 2006, and J. E. Kendrick, W. K. Huh, and R. D. Alvarez, LUMA™ Cervical Imaging System, Expert Rev. Med. Devices 4(2), 121-129, 2007, incorporated herein by reference). By illuminating the cervix at different angles and acquiring several images, the position of the glint on the surface of the cervix is different between the different images, and the images can be combined to create a glint-free combined image.

The use of polarization filters, each of which functions in the same way as a pair of polarized sunglasses, is another glint reducing or eliminating technique well known in the art (see for example, E. Hecht., Optics, Addison-Wesley, 1st edition 1972, 2nd edition 1987, 3rd edition 1997, 4th edition 2001). The polarization filter method utilizes one polarization filter placed at the light source and another filter rotated to approximately 90° positioned in front of the detector. By applying this cross polarization scheme, the reflections from the surface of the object under study are substantially minimized, if not completely eliminated, and the end result is an essentially glint-free object or image. Cross-polarization is employed, for example, in commercially available colposcopes (Welch Allyn Video Colposcope, User's manual, 2007, incorporated herein by reference), and research colposcope systems (such as described in S. Nakappan, S-Y. Park, D. Serachitopol, R. Price, M. Cardeno, S. Au, N. Mackinnin, C. MacAulay, M. Follen, and B. M. Pikkula, Methodology of real time quality control for the multispectral digital colposcope, Gynecologic Oncology 107, S21-S222, 2008, incorporated herein by reference). In these systems, the polarization filters are typically actuated by computer controlled rotating filter wheels or manually operated rotating filter holders, either on the light source side or detection side, or both. Being able to remove or rotate the polarization filters, allows for the acquisition of both cross-polarized imagery without glint and regular imagery with glint. A drawback of using manually operated or computer controlled mechanical assemblies to switch or rotate the polarization filters is the inevitable wear and tear and ultimate failure of these units over time. In addition, mechanical switch or rotational devices will introduce a delay between the image viewing or capture of cross polarized and regular imagery. During this delay, significant movement of the colposcope and/or the patient can occur. This movement can make it extremely difficult to register (align) images and track diagnostically important features, such as blood vessels of varying sizes. This is especially true for a fully automated CAD system that does not rely on human direction or intervention.

Another factor contributing to poor cervical imagery, with respect to imaging systems incorporating polarizing components, is that polarization inherently results in a loss of light. Because brightness (or intensity) is an integral part of the achievable contrast (i.e. the difference in visual properties that make an object distinguishable from other objects and the background) in the captured images, and because the contrast of an image is important in detecting cancer precursors such as vascular patterns, bright light sources are helpful in preserving the clarity of an image.

However, these bright light sources must not exceed acceptable thresholds for patient exposure to ultraviolet (UV) and infrared (IR) radiation (as described by the American Conference on Governmental Industrial Hygienists (ACGIH) in, Threshold Limit Values (TLVs) for Chemical Substances and Physical Agents and Biological Exposure Indices (BEIs), Signature Publications, 2008, incorporated herein by reference). Exposure to UV radiation has the potential of acute adverse health effects such as erythema and photokeratitis, and can cause DNA damage in the cells. Presently, the exposure to UV radiation is minimized, if not completely eliminated, by employing a UV blocking filter in the light source beam path prior to the light being available to human viewing and exposure (such as described in Welch Allyn Video Colposcope, User's manual, 2007, incorporated herein by reference) and S. Nakappan, S-Y. Park, D. Serachitopol, R. Price, M. Cardeno, S. Au, N. Mackinnin, C. MacAulay, M. Follen, and B. M. Pikkula, Methodology of real time quality control for the multispectral digital colposcope, Gynecologic Oncology 107, S21-S222, 2008, incorporated herein by reference). Many bright light sources also contain a large amount of IR which is essentially excess heat. Similar to UV radiation, the exposure to IR radiation is minimized or eliminated by the utilization of an IR blocking filter. Although the heat exposure of the user or patient is minimized or eliminated by an IR blocking filter, the heat generated by the IR radiation puts stress on the optical and mechanical components of the light source assembly and may significantly decrease the lifetime of the components, as well as of the light source itself.

Further, some bright light sources require a long start-up time before the output intensity is stable. This means there is a wait time before the device can be utilized in a clinical examination, possibly decreasing the cost-effectiveness of such a device.

A third factor contributing to poor cervical imagery is non-uniform lighting, which can lead to non-uniformity of the brightness (or intensity) in the resulting image. Non-uniformity of brightness impairs the potential accuracy of any diagnosis based on the resulting image.

The following patents may be considered relevant to the field of the present invention:

U.S. Pat. No. 4,979,498 to Oneda et al., incorporated herein by reference, discloses a video cervicoscope system for the examination of the cervix comprising: a rigid, elongated tubular member having a light guide; imaging means at the distal end of said tubular member, a disposable, light-transmitting, sleeve disposed about the distal end of said tubular member; and transmitting means to transmit an image viewed by said imaging means proximally to a control box wherein said image is received and stored.

U.S. Pat. No. 5,836,872 to Kenet et al., incorporated herein by reference, discloses a method for monitoring a region of a body surface which includes recording at a first time a first multispectral digital image of the surface including the region, recording at a subsequent time a subsequent multispectral digital image of the surface including the region, and comparing the first and the subsequent images. Also, such a method in which the first and subsequent images are high magnification images, and further including recording low magnification images that include the high magnification images. Also disclosed is a method for forming a diagnostically useful classification of pigmented skin lesions, using such a method to construct a database containing quantitatively extracted selected features from images recorded from a plurality of skin lesions, and correlating the features from each such lesion in the database with the medical history of the skin lesion from which the image was recorded. Further, a method for diagnosis of a premelanomatous or early melanomatous condition includes using the method for characterizing a surface region including the lesion and comparing the features of the lesion so obtained with the features in a database obtained from a number of skin lesions including lesions known to be premelanomatous or early melanomatous, or classifying the features of the lesion according to the diagnostically useful classification of pigmented skin lesions.

U.S. Pat. No. 5,929,443 to Alfano et al., incorporated herein by reference, discloses a method and apparatus for the imaging of objects based on the polarization and depolarization of light. In one embodiment, a surface of a turbid medium is imaged by illuminating the surface of the turbid medium with light, whereby light is backscattered from the illuminated surface of the turbid medium, detecting a pair of complementary polarization components of the backscattered light, and forming an image of the illuminated surface using the pair of complementary polarization components. The illuminating light is preferably polarized (e.g., linearly polarized, circularly polarized, elliptically polarized), where, for example, the illuminating light is linearly polarized, the pair of complementary polarization components are preferably the parallel and perpendicular components to the polarized illuminating light, and the image is formed by subtracting the perpendicular component from the parallel component, by taking a ratio of the parallel and perpendicular components or by using some combination of a ratio and difference of the parallel and perpendicular components.

U.S. Pat. No. 5,989,184 to Blair, incorporated herein by reference, discloses an apparatus for digital colposcopy and videography which comprises a digital imaging camera that is operably coupled to the optical path of the digital colposcope by means of a beam splitter so that a digital image of the cervico-vaginal tissue can be captured. The digital imaging camera and digital colposcope are mounted to one end of an articulating arm of the apparatus. Digital processing means is operably connected to the digital imaging camera to create a digital image. The digital processing means is housed in a stand of the assembly.

U.S. Pat. No. 6,277,067 to Blair, incorporated herein by reference, discloses a method and portable apparatus for the visual examination and grading of cervical epithelium by means of a hand-held colposcopy assembly capable of producing a digital image of the cervix. The apparatus enables real-time imaging and archiving of images of the entire cervix for the purpose of detecting cancerous and pre-cancerous tissue, and by virtue of computerized image processing, suggests an objective diagnosis of the cervical epithelium by means of a low cost, portable, hand-held digital colposcope.

U.S. Pat. No. 6,587,711 to Alfano et al., incorporated herein by reference, discloses an apparatus for examining an object, such as skin, mucosa and cervical tissues, for the purpose of detecting cancer and precancerous conditions. In one embodiment, the apparatus includes a gun-shaped housing having a handle portion and a barrel portion. The front end of the barrel portion is open, and a glass cover is mounted therein. Red, green, blue, and white LED's are disposed within the handle portion of the housing, and are electrically connected to a battery and are also disposed within the handle portion of the housing. A manually-operable switch for controlling actuation of each of the four LED's is accessible on the handle portion of the housing. An optical fiber is disposed inside the housing and is used to transmit light from the four LED's through a first polarizer disposed in the barrel portion of the housing and then through the glass cover to illuminate a desired object. Reflected light from the object entering the housing through the glass cover is passed through a second polarizer, which is adjustably mounted in the barrel portion of the housing and which is preferably oriented to pass depolarized light emitted from an illuminated object, and is then imaged by optics onto a black and white CCD (charged coupled device) detector (camera). The optics may include a lens that is disposed within the barrel portion and is adjustably spaced relative to the CCD detector. The detector is coupled to a wireless transmitter mounted in the housing, the transmitter transmitting the output from the detector to a remotely located wireless receiver. The wireless receiver is coupled to a computer, which then processes the output from the detector. The processed output is then displayed on a display. The display may be remotely situated for remote expert diagnosis.

U.S. Pat. No. 6,766,184 to Utzinger et al., incorporated herein by reference, discloses methods and apparatus for generating multispectral images of tissue. The multispectral images may be used as a diagnostic tool for conditions such as cervical cancer detection and diagnosis. Primary radiation is produced with an illumination source. The primary radiation is filtered to select a first wavelength and a first polarization. Tissue is illuminated with the filtered primary radiation to generate secondary radiation, which is filtered to select a second wavelength and a second polarization. The filtered secondary radiation is collected with a detector, and a plurality of multispectral images of the tissue is generated according to different combinations of first and second wavelengths and first and second polarizations with an analysis unit in operable relation with the detector. Apparatus utilizing the invention include endoscopes and colposcopes.

U.S. Patent Application Publication No. 2006/0141633 to Balas, incorporated herein by reference, discloses a method and an apparatus for the in vivo, non-invasive, early detection of alterations and mapping of the grade of these alterations, caused by the biochemical and/or the functional characteristics of epithelial tissues during the development of tissue atypias, dysplasias, neoplasias and cancers. The method is based on the simultaneous measurement of the spatial, temporal and spectral alterations in the characteristics of the light that is re-emitted from the tissue under examination, as a result of a combined tissue excitation with light and special chemical agents. The topical or systematic administration of these agents results in an evanescent contrast enhancement between normal and abnormal areas of tissue. The apparatus enables the capturing of temporally successive imaging in one or more spectral bands simultaneously. Based on the measured data, the characteristic curves that express the agent-tissue interaction kinetics, as well as numerical parameters derived from these data, are determined in any spatial point of the examined area. Mapping and characterization of the lesion are based on these parameters.

U.S. Patent Publication No. 2006/0184043 to Tromberg et al., incorporated herein by reference, discloses an improvement in a method for quantitative modulated imaging to perform depth sectioned reflectance or transmission imaging in a turbid medium, such as human or animal tissue. The method is directed to the steps of encoding a periodic pattern of illumination, preferably with a fluorescent excitation wavelength when exposing a turbid medium to the periodic pattern, to provide depth-resolved discrimination of structures within the turbid medium; and reconstructing a non-contact three dimensional image of the structure within a turbid medium. As a result, wide field imaging, separation of the average background optical properties from the heterogeneity components for a single image, separation of superficial features from deep features based on selection of spatial frequency of illumination, or qualitative and quantitative structure, function and composition information, is extracted from spatially encoded data.

U.S. Patent Application No. 2006/0215406 to Thrailkill, incorporated herein by reference, discloses a medical diagnostic instrument, which could be a colposcope for examining cervical tissue, and includes a light source comprising an annular array of high intensity light emitting diodes (LEDs). The LED array includes a central access opening which provides viewing access for the colposcope optical components to the illumination site. The array includes a plurality of sets of LEDs, with each set including a red, blue and green emitting LED. The intensities of the red, blue and green LEDs, respectively, are controllable with a controller to continuously vary or tune the spectral characteristics of the illumination from the light source. Selected color mixes can be stored in a memory for later retrieval.

U.S. Patent Publication No. 2007/0213590 to Squiccinarini, incorporated herein by reference, discloses a portable multi-functional endoscopic device and method for use in the examination of tissue to permit diagnostic, therapeutic or anatomical assessment data to be transmitted, recorded, or analyzed. The device includes a base unit sized and configured to be held in a human hand to permit functional and directional control of the device, an interchangeable head assembly sized and configured to be inserted into an orifice being removably connectable to the base unit, and an inflatable tissue stabilizer disposed external to a distal end of the device. In preferred aspects, the endoscopic device has an image sensor, light source, lens, air pump, and working tools.

U.S. Patent Application No. 2008/0049997 to Chin, incorporated herein by reference, discloses an image enhancement system that includes a data source which provides image data of an object, enhancement data storage including image enhancement information, an image enhancement unit configured to enhance the image data based on the image enhancement information, and a color display configured to display a monochrome image representing the enhanced image data on a screen thereof. The enhanced image data may include a gray level scale of at least 32 bits per pixel.

U.S. Patent Application Publication No. 2005/004365 to Zelenchuk, incorporated herein by reference, discloses a system and method for the in situ discrimination of healthy and diseased tissue. A fiberoptic probe is employed to direct ultraviolet illumination onto a tissue specimen and to collect the fluorescent response radiation. The response radiation is observed at three selected wavelengths, one of which corresponds to an isosbestic point. In one example, the isosbestic point occurs at about 431 nm. The intensities of the observed signals are normalized using the 431 nm intensity. A score is determined using the ratios in a discriminant analysis. The tissue under examination is resected or not, based on the diagnosis of disease or health, according to the outcome of the discriminant analysis.

DISCLOSURE OF THE INVENTION

The present invention addresses the problem of glint inherent in performing a standard colposcopic exam and addresses the limitations of using mechanical filter wheels or rotating filter assemblies, the brightness of the light source, the health aspects of exposure to UV and IR hazards, and the extended start-up time of most bright light sources by employing a non-mechanical, non-moving (fixed or stationary) polarization assembly with an electronically switchable light source system based on high-intensity light emitting diodes (LEDs), which do not to generate any UV or IR radiation.

The present invention is a device that preferably creates pairs of clear images, a glint-free image (cross-polarized image) and an image with glint (parallel-polarized image), at multiple magnifications. The term cross-polarized (XP) refers to when a first polarization orientation is perpendicular to a second polarization orientation, whereas the term parallel-polarized (PP) refers to when a first polarization orientation is parallel to a second polarization orientation. In the present invention, PP can also mean singly-polarized, where there is only one polarization orientation, or unpolarized. The XP and PP images can be used in conjunction with each other for diagnostic purposes. For example, XP and PP images can be registered (aligned) and then faded into each other to aid a clinician in cancer detection (as described in co-pending, commonly assigned U.S. patent application Ser. No. 12/228,298, entitled "A Method of Image Manipulation to Fade Between Two Images" filed Aug. 11, 2008, incorporated herein by reference). Fading between the two images allows a clinician to detect important features that may be masked by glint, while at the same time retaining to a desired extent the natural and three-dimensional shape of tissue or an organ (such as the cervix) in the image.

To suppress glint, the first preferred embodiment preferably employs cross-polarization, which allows for deeper layers of tissue to be visualized at multiple magnifications, thereby further enhancing the invention's diagnostic capabilities. To produce a brighter and more uniform illuminated surface with a denser light emission than typical fluorescent and incandescent light sources, the light source in this embodiment preferably includes two sets of multiple light-emitting diodes (LEDs), which are preferably turned on and off rapidly by electronically changing the operating current or voltage, to directly and uniformly illuminate a field of view. The light from the LEDs is preferably polarized through an illumination polarizer before reaching the field of view.

The present invention's use of LEDs offers several benefits. LEDs, unlike fluorescent and incandescent lights, are solid-state components, allowing for faster switching on and off, so that switching between parallel-polarized image acquisition and cross-polarized image acquisition can be achieved more easily and quickly. The invention preferably uses fixed illumination polarizers (IP) in front of the two sets of LEDs, instead of mechanically moving polarizing filters. Rapidly switching between the LEDs (rapidly alternating each set of LEDs on and off) also reduces the influence from patient movement between successive images, allowing for better registration (alignment) between successive images and improving the possibility of detection of diagnostically important features. An LED assembly is also less expensive and more compact than the typical illumination sources using either fluorescent or incandescent lighting with bundles of fiber optic cables, and LEDs are also more reliable than using either fluorescent or incandescent lights because they are rated for approximately 50,000 hours of use and one million on/off cycles. As a comparison, the rated lifetimes for fluorescent or incandescent lights are typically less than 10,000 hours with many having a typical lifetime of only 1000 hours. LEDs also generate less heat than fluorescent and incandescent lights. Therefore, less cooling and less thermal insulation are required for the device housing, allowing for smaller power supplies—e.g., smaller fans that produce less noise and vibration for patient and operator comfort. The thermal efficiency of LEDs also reduces heat, which generates thermal expansion of the device's mounts and can degrade the optical quality of the images. LEDs also require less power and are more efficient in converting electrical power consumption to visible light, ultimately reducing the power consumption of the device, and enabling battery operation in remote areas, if necessary. Further, light emitted by an LED is also emitted over a broad flat area unlike conventional incandescent and fluorescent lights, thus providing for more uniform illumination.

Moreover, as patient safety is of utmost importance in in vivo examinations, the fact that the spectral emission of LEDs, unlike fluorescent lights, does not contain a significant amount of ultraviolet (UV) light is extremely beneficial. This fact eliminates the need for the present invention to utilize UV filters, detectors and hardware, all of which are used in conjunction with UV emitting light sources to monitor, measure, control, or minimize UV output to prevent UV damage to the examined region.

The inventors are unaware of any other imaging device that incorporates the advantages of rapidly switching between different sets of LEDs to instantly, directly, and uniformly illuminate a field of view for near-simultaneous imaging of tissue or an organ; and cross-polarization to suppress the negative effects of glint without compromising the brightness of the image(s).

The first presently preferred embodiment of the invention preferably uses two sets of LEDs. Each LED in a set has a separate non-moving (fixed or stationary) illumination polarizer (IP) in front of it, with the fixed IP in front of each of the LEDs in the first set having a horizontal orientation or being horizontally-polarized (it does not have to be a horizontal orientation but can be any first polarization orientation), and the fixed IP in front of each of the LEDs in the second set having a vertical orientation or being vertically-polarized (it does not have be a vertical orientation but can be any second polarization orientation which is substantially perpendicular to the first polarization orientation). Preferably, the IPs are integrally formed into a single polarizing element, with each LED in a set placed behind a corresponding region having the appropriate polarization.

The present invention also preferably includes an additional separate polarizing element, preferably a polarizing beam splitter (PBS), which simultaneously polarizes and splits an incident beam of light into two beams and directs the split beams towards two cameras (detectors), so that each camera receives a differently polarized image of the examined region. Ideally, a polarizing beamsplitter splits the beam into two beams that have orthogonal (perpendicular) polarizations so that the horizontally-polarized light (or light having a first polarization orientation) reflects off the PBS and is directed toward one camera, and vertically-polarized light (or light having a second polarization orientation) is transmitted through the PBS toward the second camera.

Thus, when the first set of LEDs is turned on, the light passes through an IP to become horizontally-polarized light (or light having a first polarization orientation) which directly illuminates a subject (such as tissue or an organ) in the field of view. Part of the horizontally-polarized light reflects off the subject as horizontally-polarized glint (described below), while the other part is partially absorbed by the subject and then reflected as diffuse reflected light (described below). The reflected glint maintains its horizontal polarization (or first polarization orientation) to become horizontally-polarized glint (or glint having a first polarization orientation). The light that penetrates the tissue will gradually become unpolarized after a sufficient number of scattering events, and a portion will be reflected from the tissue as diffuse reflected light. The first total reflected light reflected by the subject thus contains horizontally-polarized glint (or glint having a first polarization orientation) and diffuse reflected light. While glint refers to light that is reflected off one surface (e.g., the surface of the cervical tissue) in one direction (e.g., towards one of the cameras), diffuse light refers to light that is scattered in all directions and is unpolarized. It is well known in the art that unpolarized light can be described as a combination of both PP and XP light. Because a camera captures only that portion of the diffuse light that is reflected in the camera's direction, the diffuse reflected light does not have the same visually-impairing effect (i.e., glare) on the image as glint.

When the first total reflected light reaches the PBS, that beam splitter both polarizes and splits the light into first and second beams of light which contain substantially perpendicular polarization orientations to one another. The PBS preferably directs the horizontally-polarized glint and any other diffuse reflected light that has a horizontal orientation (a first PP output) to a first camera which creates a first PP image. The second beam of light split by the PBS contains any diffuse reflected light with a polarization orientation that is substantially perpendicular to the first beam (a first XP output) and is directed to a second camera which creates a first XP image. For all preferred embodiments of the invention, the PP image will always be created from the split beam of light which contains glint, whereas the XP image will be created from the split beam of light that does not contain glint.

Alternatively, when the second set of LEDs is turned on, the light passes through an IP to become vertically-polarized light (or any light having a second polarization orientation, where the second polarization orientation is substantially perpendicular to the first polarization orientation). This time, the second total reflected light will contain vertically-polarized glint (or glint having a second polarization orientation) and diffuse reflected light. The PBS will now split the second total reflected light into a second PP output and a second XP output, and direct the second PP output (vertically-polarized glint and any diffuse reflected light that has a vertical orientation) to the second camera which creates a second PP image. The second XP output (any total reflected light that has a horizontal orientation) will be directed by the PBS to the first camera to create a second XP image.

The two cameras are preferably CCD (charged coupled device) or CMOS (complimentary metal oxide semiconductor) cameras that are co-aligned (aligned with each other) but have different magnifications. The first camera preferably has a first magnification (a full-view or a magnification that allows the entire subject of interest to be imaged), and the second camera preferably has a second magnification (a magnified view or a magnification that allows for the viewing of the smallest diagnostically important features). By rapidly switching between the two sets of LEDs (by rapidly switching one set on and the other set off, and vice versa), the two cameras in the device will acquire four separate images of the same examined region, two images at a first magnification, and two images at a second magnification. Of the two images at a first magnification, one image will be parallel-polarized and the other will be cross-polarized. The same applies to the two images at a second magnification: one will be parallel-polarized and the other will be cross-polarized.

Rapidly switching between the two sets of LEDs by electronically turning their operating current on and off, allows for near-simultaneous acquisition of images that are co-registered (co-aligned) by the two cameras and controls whether the imaging system captures parallel- or cross-polarized images, and at what magnification the images are captured by the cameras. PP images will resemble standard colposcopic images, and although XP images will be visually blurrier, they will lack the glint present in the PP images.

A second preferred embodiment comprises two sets of LEDs and uses one camera at a single level of magnification or continuous magnification by the use of a zoom lens. In this second preferred embodiment, by rapidly switching between the two sets of LEDs, after passing the unpolarized light through an IP, the device will acquire two near simultaneous images with the same magnification of the same examined region, one XP and one PP image. Although the use of a zoom lens involves a mechanical movement of optical components with an associated time delay, it would allow for the acquisition of XP and PP image pairs with different magnifications.

A third preferred embodiment is a simpler system which is similar to the first embodiment, but includes only one set of LEDs, and uses two cameras. In this preferred embodiment, unpolarized light from the single set of LEDs is polarized when it passes through an IP to create horizontally-polarized light (or light having a first polarization orientation) to directly and uniformly illuminate a subject in a field of view. The horizontally-polarized light that interacts with the subject is reflected as total reflected light that includes horizontally-polarized glint and diffuse reflected light. When the total reflected light reaches the PBS, the PBS preferably directs the horizontally-polarized glint and any diffuse reflected light having a horizontal orientation (PP output), to the first camera which creates the PP image, and directs any diffuse reflected light having a vertical orientation (XP output) to the second camera which creates the XP image. By adding zoom control to the cameras, PP and XP images at different magnifications can be acquired.

A fourth preferred embodiment is simpler than all of the previously described embodiments. It uses only one set of LEDs and one camera. The fourth preferred embodiment emphasizes the collection of glint-free (XP) images only. Again, the device polarizes unpolarized light from the single set of LEDs by passing the unpolarized light through an IP to create horizontally-polarized light (or light having a first polarization orientation) to illuminate a subject in a field of view. The horizontally-polarized light that interacts with the subject is reflected as total reflected light that includes horizontally-polarized glint and diffuse reflected light. When the total reflected light reaches the PBS, it directs any diffuse reflected light having a vertical orientation (XP output) to the camera which creates the XP image. By adding zoom control to the camera system, XP images at different magnifications can be acquired.

The presently preferred embodiment of the invention also includes a focusing subsystem (as described in co-pending, commonly assigned U.S. patent application Ser. No. 12/221, 267, entitled "Single Spot Focus Control" filed Jul. 31, 2008, incorporated herein by reference) that utilizes the vertical position of a focused beam of light (from e.g. a laser beam) to assess the distance between the device and the examined region, in order to achieve optimal focus. Preferably, the two cameras are able to operate in video mode (lower resolution but faster image capture) and camera mode (maximum resolution at a lower image capture rate for the acquisition high-resolution imagery with all of the diagnostically features present). The focusing subsystem is preferably utilized in video mode to achieve satisfactory focus before the invention collects the XP and PP images in camera mode.

The presently preferred embodiment of the invention also includes a data management system that allows for a completely digital data flow, simplifying data transfer and storage, and minimizing the risk of human error. The data management system allows for (i) the use of image-enhancement algorithms; (ii) the use of image-processing algorithms; (iii) the use of annotation programs; (iv) digital archiving; and (v) remote viewing. This also allows the invention to (i) perform system diagnostics; (ii) present more comprehensive system information to the operator and technicians; and (iii) include comprehensive information, with respect to each image data set, about the state of the system when the images were acquired. It also preferably contains a fully integrated user interface, in which physical buttons are tied to the hardware and software platforms, permitting the functionality of the device to be adapted, if necessary, to new functions. A data management system with similar features is described in co-pending, commonly assigned U.S. patent application Ser. No. 11/184,046 entitled "Uterine Cervical Cancer Computer-Aided Diagnosis", filed on Feb. 3, 2005, incorporated herein by reference.

The present invention is also preferably a self-contained system, meaning it is unnecessary to switch between a colposcope and a physically separate computer to review and annotate images, and the system eliminates cable bundles that would otherwise be present between a colposcope and a computer.

The presently preferred embodiment of the invention also discloses a process of creating polarized light; illuminating a field of view with the polarized light; reflecting the polarized light off a subject in the field of view; splitting the reflected light into parallel-polarized and cross-polarized outputs; producing a parallel-polarized image from the parallel polarized output and a cross-polarized image from the cross-polarized output; and using the parallel polarized image and cross-polarized image to enhance the visualization of tissue.

BRIEF DESCRIPTION OF DRAWINGS

FIGS. 2A, 2B and 2C are conceptual front views of the illumination system illustrating the configuration for two sets of LEDs.

FIGS. 3A, 3B, and 3C are conceptual front views of the illumination system illustrating the configuration for one set of horizontally-polarized (or having a first polarization direction) LEDs.

FIGS. 4A, 4B, and 4C are conceptual front views of the illumination system illustrating the configuration for one set of vertically-polarized (or second polarization direction) LEDs.

FIGS. 5A and 5B are conceptual views of the preferred embodiment to illustrate the process of cross-polarization.

In FIG. 8A, the cervix is in focus, in FIG. 8B, the cervix is too close, and in FIG. 8C, the cervix is too far.

BEST MODE FOR CARRYING OUT THE INVENTION

Figure 1:
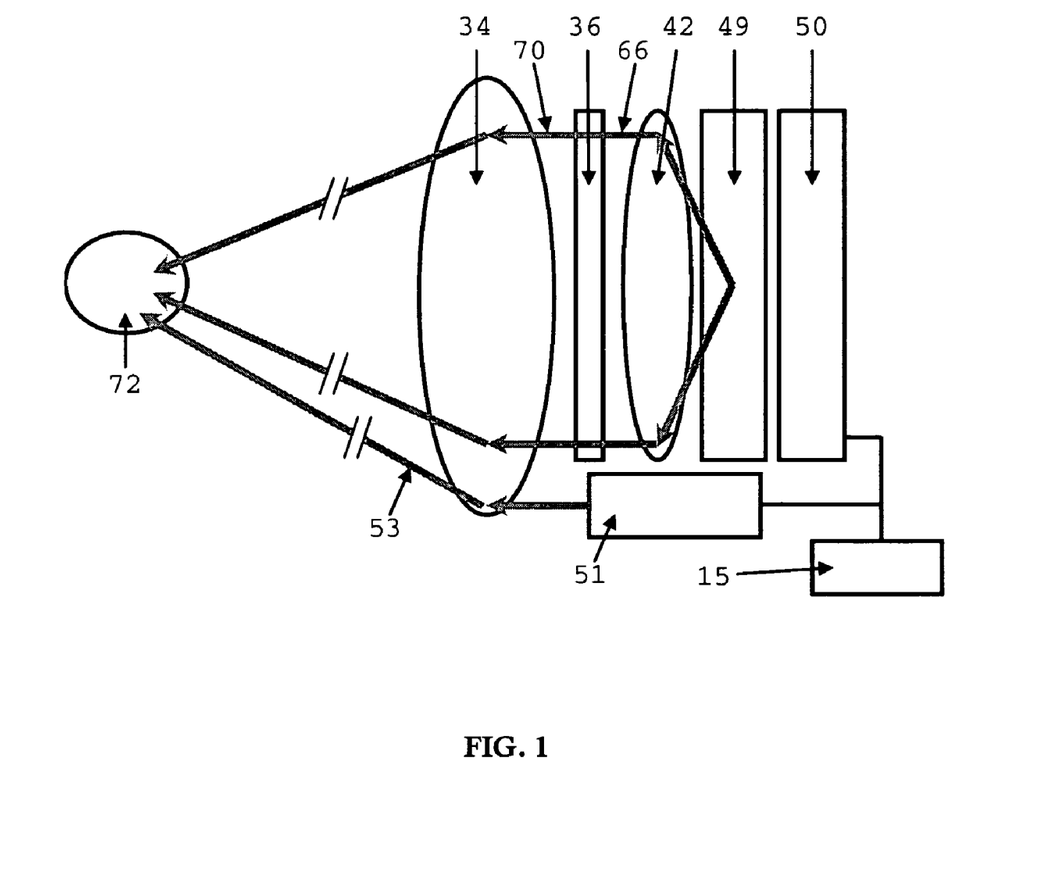
FIG. 1 is a conceptual side view of the main components of the illumination system.

Initially, a subject 72 (such as an organ or tissue) in a field of view is directly illuminated by the presently preferred embodiment's illumination subsystem, as shown in FIG. 1. The purpose of the illumination subsystem is to provide even and direct illumination of the subject in the field of view with sufficient intensity (brightness) for the invention to acquire images quickly enough to avoid or minimize blur due to motion (for e.g. patient movement). The illumination subsystem preferably comprises the following main components: (a) front lens 34, (b) illumination polarizer (IP) 36, (c) LED lenses 42, (d) one or more sets of LEDs 49, (e) illumination board 50 with control electronics and (f) power supply 15. The laser 51 of the focusing system is also shown, as is the subject 72 being illuminated, and the light beam direction 70 of the illumination system. The LEDs 49 are preferably mounted onto the illumination board 50, which also provides control electronics to set the operating current and voltage, and to rapidly turn the LEDs 49 on and off. The LED lenses 42 focus the divergent light from the unpolarized LED 49 into light output beams 66. An IP 36 is placed in front of the LED lenses 42. The front lens 34 directs the polarized LED light output 70 towards the subject 72 to illuminate the entire field of view that contains the subject 72.

Figure 2A:
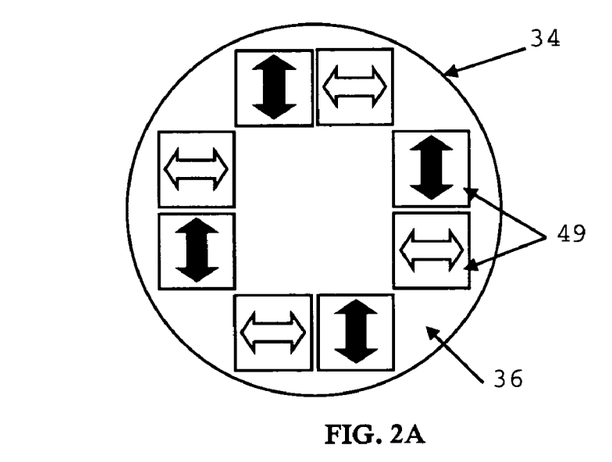
FIG. 2A shows a configuration containing a total of 8 LEDs.
Figure 2B:
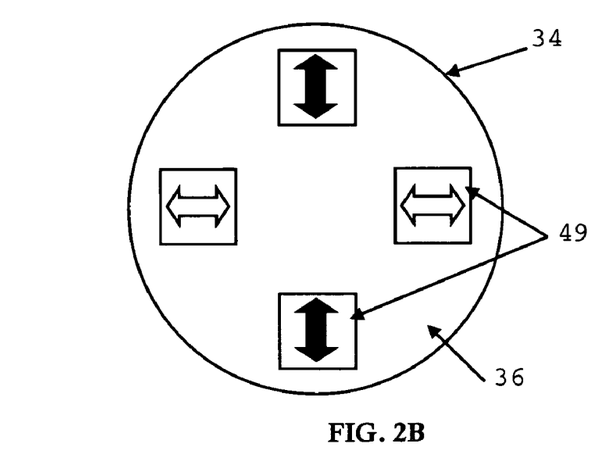
FIG. 2B shows a configuration containing a total of 4 LEDs.
Figure 2C:
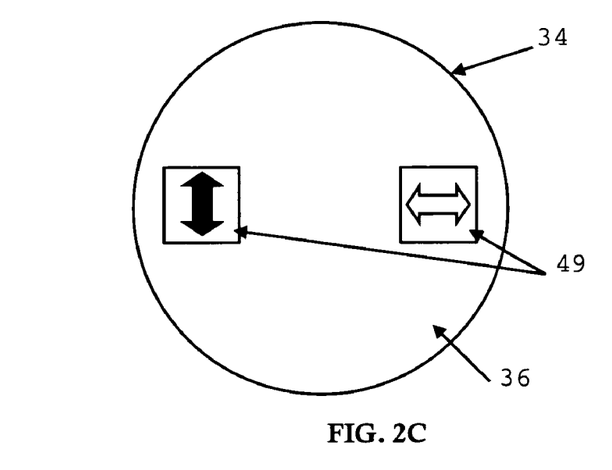
FIG. 2C shows a configuration containing a total of 2 LEDS.
Figure 3A:
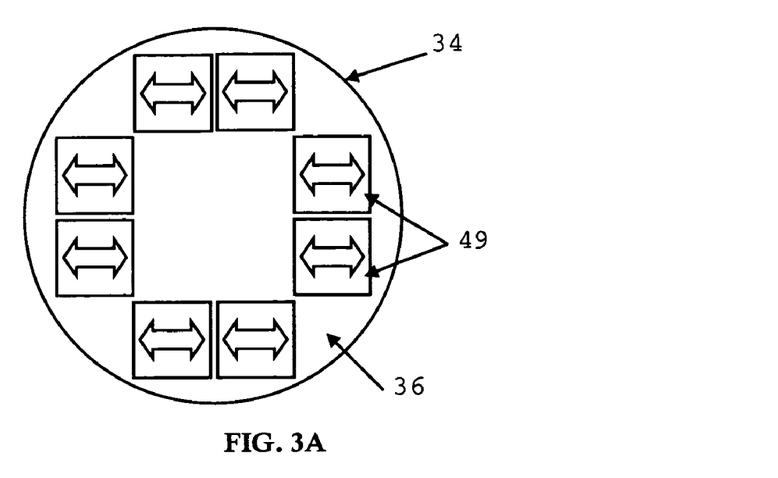
FIG. 3A shows a configuration containing a total of 8 LEDs.
Figure 3B:
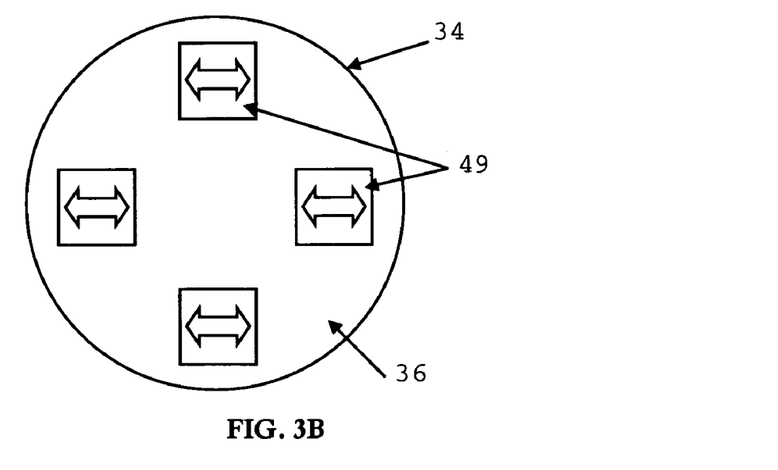
FIG. 3B shows a configuration containing a total of 4 LEDs.
Figure 3C:
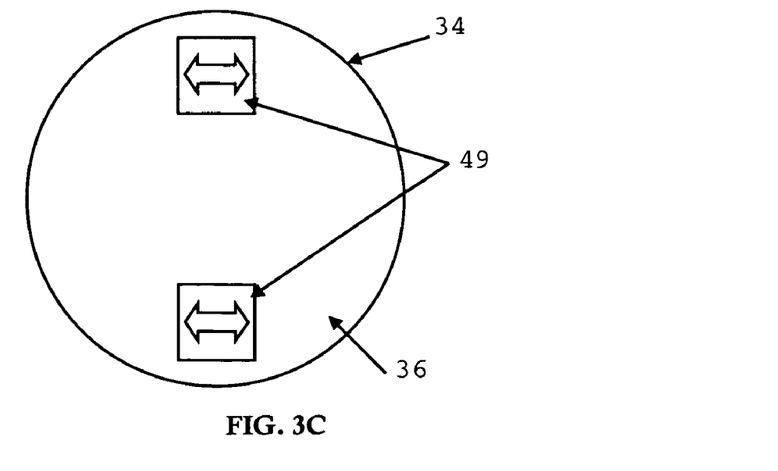
FIG. 3C shows a configuration containing a total of 2 LEDS.
Figure 4A:
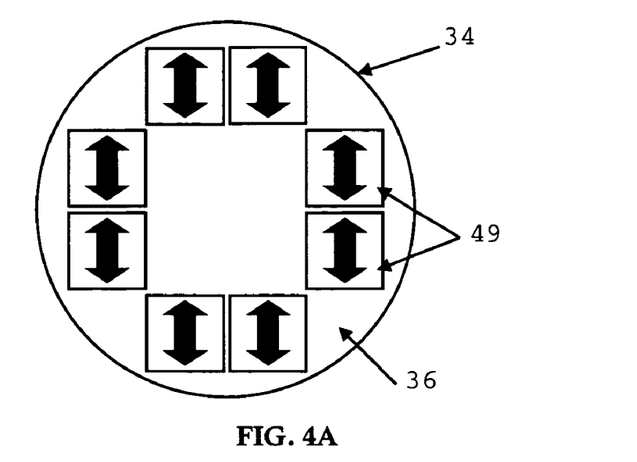
FIG. 4A shows a configuration containing a total of 8 LEDs.
Figure 4B:
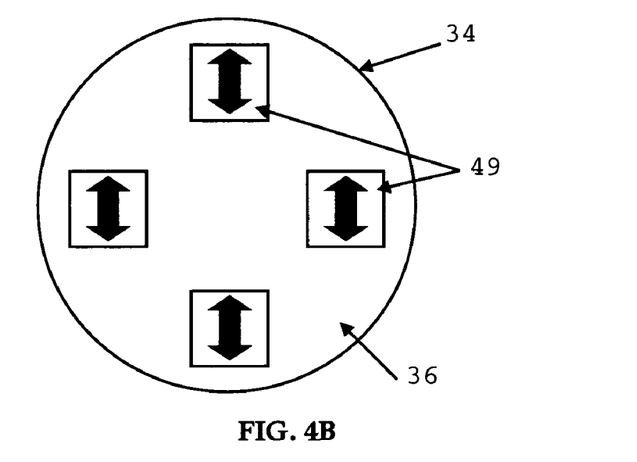
FIG. 4B shows a configuration containing a total of 4 LEDs.
Figure 4C:
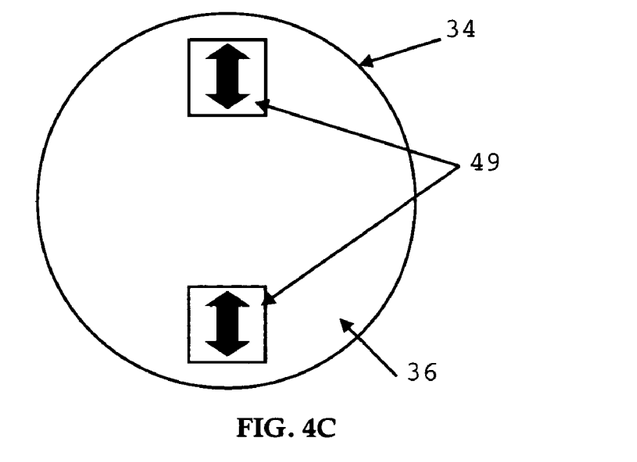
FIG. 4C shows a configuration containing a total of 2 LEDS.

Front views of the illumination system showing the LEDs 49, IP 36, and front lens 34 are displayed in FIG. 2A-2C, FIG. 3A-3C, and FIG. 4A-4C. Configurations for two sets of LEDs are illustrated in FIG. 2A-2C whereas configurations for one set of LEDs are illustrated in FIG. 3A-3C and FIG. 4A-4C. The polarizing direction of the light is indicated by the arrows.

FIGS. 2A-2C illustrate the preferred embodiment using two sets of LEDs 49, the solid arrows designating the first set of LEDs 49 and the outlined arrows designating the second set of LEDs 49. The direction of the arrows designates the polarization orientation of the LED light 70 after being transmitted by the IP 36. The outlined arrows have a horizontal polarization orientation (or a first polarization orientation), and the solid black arrows have a vertical orientation (or a second polarization orientation). For two sets of LEDs 49, the IP 36 is preferably designed to polarize the light from each set of LEDs 49 such that the second polarization orientation is substantially perpendicular to the first polarization orientation. FIG. 2A, FIG. 2B, and FIG. 2C illustrate the use of 8, 4, and 2 LEDs, respectively, to achieve illumination with light of perpendicular polarization orientations. For two sets of LEDs 49 with perpendicular polarization orientations (i.e. two polarization orientations), the configuration will preferably be designed with the total number of LEDs as a multiple of 2 to ensure similar intensity (brightness) and uniform illumination for both polarization orientations. Although not shown in FIG. 2A-2C, a person of ordinary skill in the art could easily design the LED configuration for additional LEDs, such as 6, 10, 12, 14, etc. The circular design and alternating polarization orientation of the LEDs 49 will ensure uniform illumination for both polarization orientations.

FIGS. 3A-3C and FIGS. 4A-4C, illustrate an alternative embodiment which uses only one set of LEDs 49, the direction of the arrows again designating the polarization orientation of the light from the LED. Here, the IP 36 is designed to polarize the light from the LEDs 49 in a single polarization orientation only. FIG. 3A, FIG. 3B and FIG. 3C, and FIG. 4A, FIG. 4B and FIG. 4C illustrate the use of 8, 4, and 2 LEDs, respectively. Here any number of LEDs can be used; however, a circular configuration will again ensure uniform illumination. Again, a person of ordinary skill in the art could easily design the LED configuration for a number of LEDs other than 2, 4, and 8 (for example, 6, 10, 12, 14, etc.).

Figure 5A:
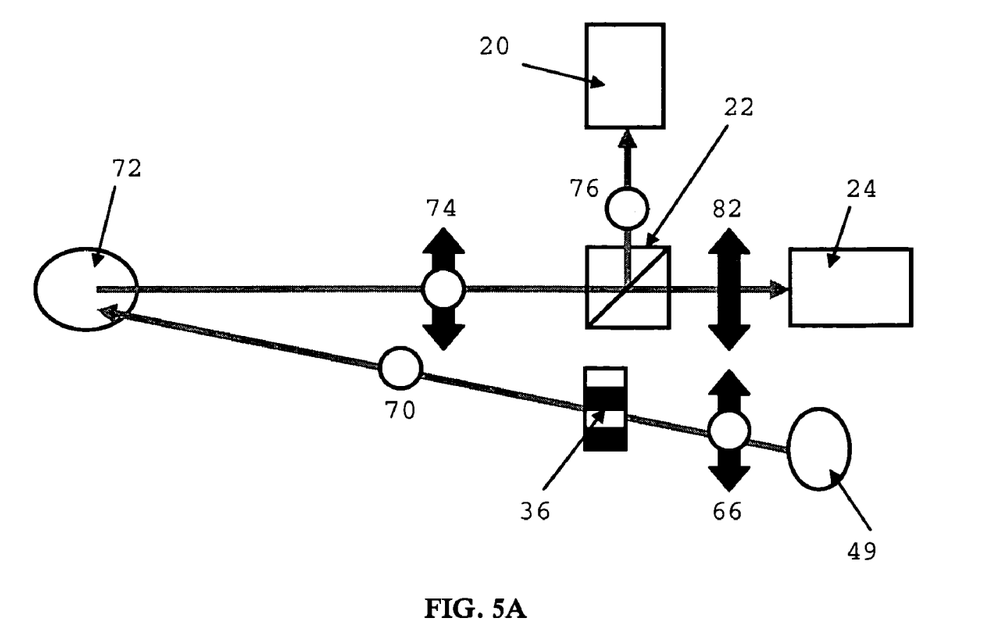
FIG. 5A shows a two camera system and FIG. 5B shows a single camera system.
Figure 5B:
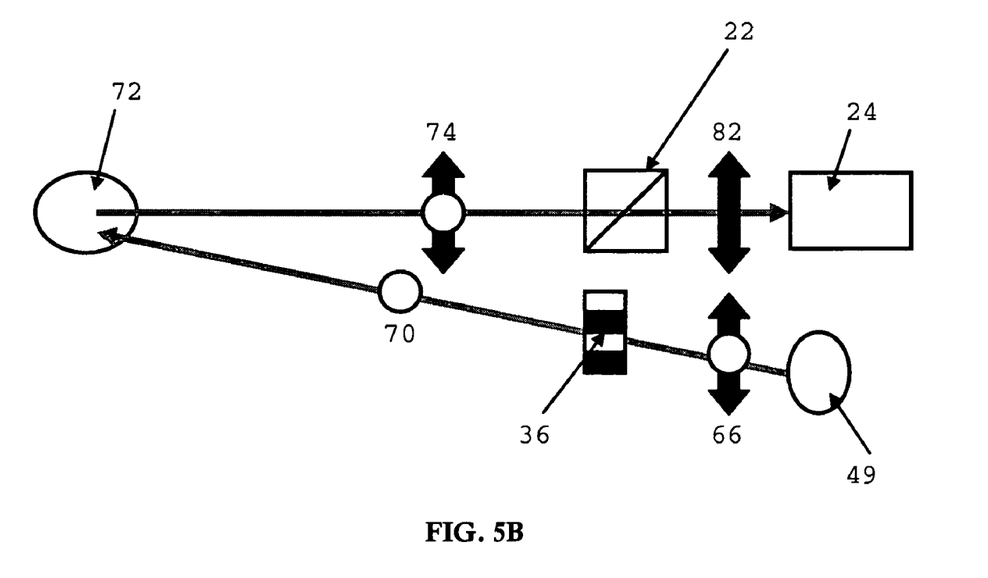

FIG. 5A and FIG. 5B illustrate the process of cross-polarization in the preferred embodiment of the invention. The presence of light with a polarization orientation perpendicular to the plane of the paper (horizontally-polarized light) is indicated by an "O" (e.g. 70), and the presence of light with a polarization orientation parallel to the plane of the paper (vertically-polarized light) is indicated by an up and down arrow (e.g. 82). The presence of both an "O" and an up and down arrow denotes unpolarized light (e.g. 66).

As illustrated in FIG. 5A, XP and PP images are obtained by illuminating a field of view with unpolarized light 66 from at least one set of LEDs 49, which is filtered through an IP 36 to produce horizontally-polarized light (or any light having a first polarization orientation) 70. When the horizontally-polarized light 70 interacts with a subject 72 (such as cervical tissue) in the field of view, it partially penetrates the tissue, and is also partially reflected as horizontally-polarized glint (or glint having a first polarization orientation). A portion of the light that penetrates the tissue will gradually become unpolarized, and reflect from the tissue as diffuse reflected light. The total reflected light 74 will be a combination of both (i) the horizontally-polarized glint, and (ii) the diffuse reflected light. When the total reflected light 74 reaches an additional polarizing element designed to split the light into perpendicular orientations (such as a polarizing beam splitter or PBS 22), it splits the total reflected light into a PP output 76 and a XP output 82 that are received by separate cameras 20 and 24. The PP output creates the PP image, and contains horizontally-polarized glint and any diffuse reflected light having the same polarization (horizontally-polarized diffuse reflected light). The PP image will look substantially similar to standard colposcopic data. The other output, the XP output, is vertically-polarized (vertically-polarized does not mean the light has to be vertically-polarized but can be any light having a second polarization orientation that is at a substantial angle to the first polarization described above, preferably substantially perpendicular), and contains only the diffuse reflected light having the same vertical-polarization, but no glint. Thus, a first camera 20 creates a PP image and a second camera 24 creates the XP image.

FIG. 5B illustrates the concept of using one camera 24 only and, thus, acquiring an XP image only.

Figure 6A:
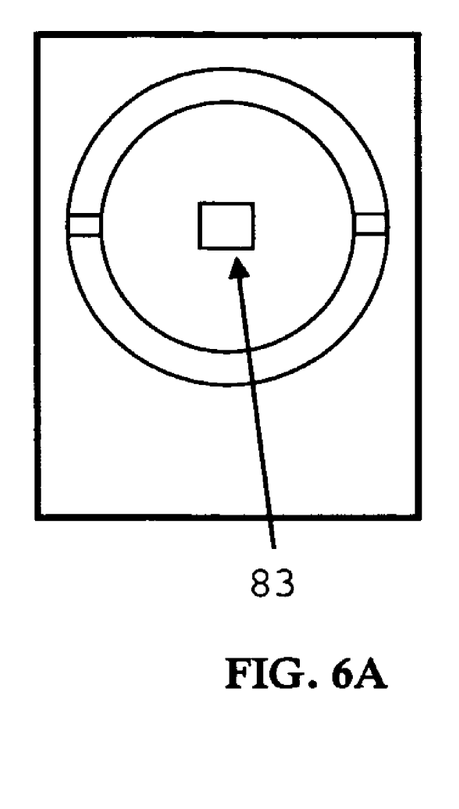
FIG. 6A is a front view of one of the camera systems.
Figure 6B:
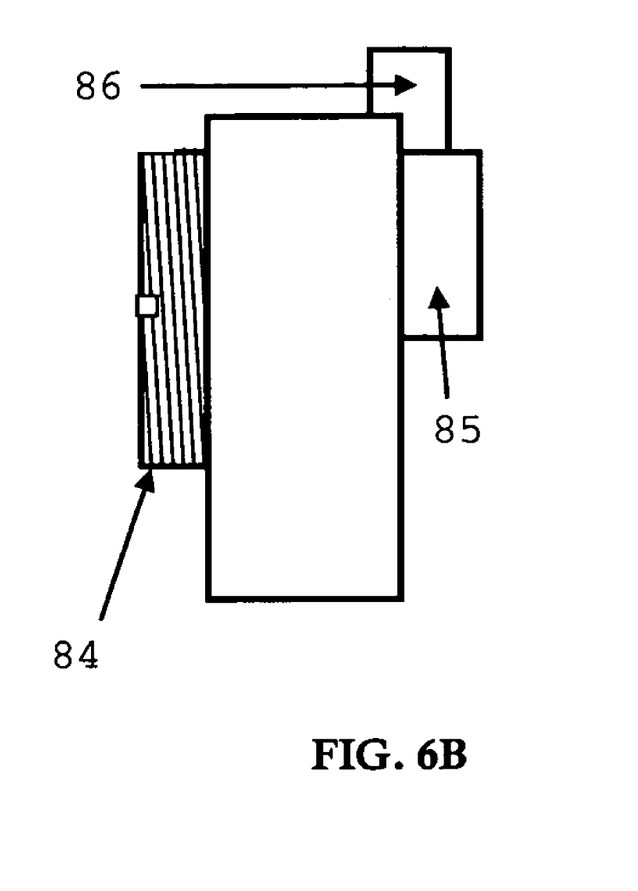
FIG. 6B is a side view thereof.
Figure 7A:
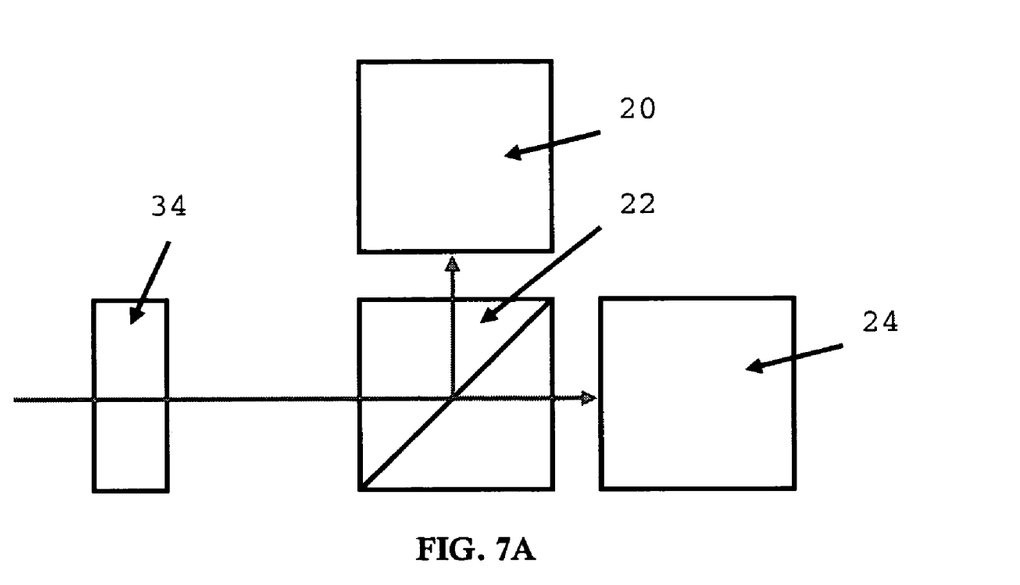
FIG. 7A is a side conceptual view of the detection system for a two camera system.
Figure 7B:
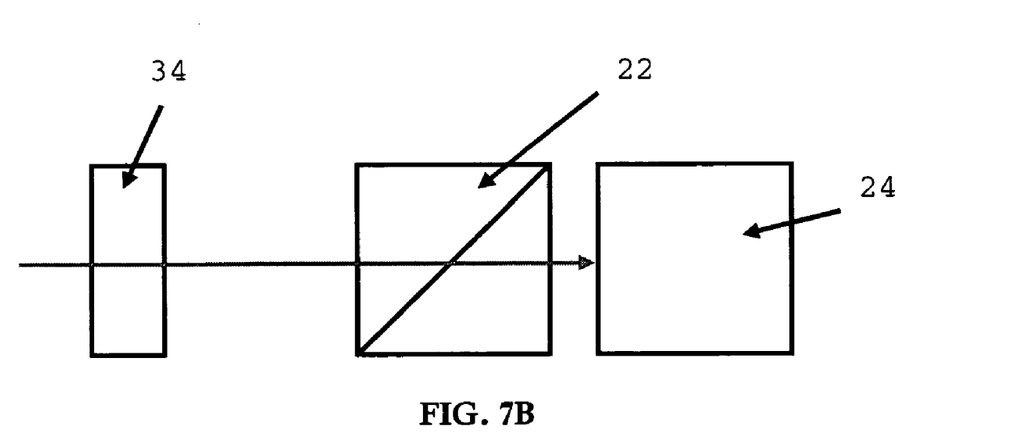
FIG. 7B is a side conceptual view of the detection system for a one camera system.

FIG. 6A and FIG. 6B illustrate the camera configuration of the presently preferred embodiment. FIG. 6A is a front view of one of the cameras and FIG. 6B is a side view thereof. As seen in FIGS. 6A and 6B, each camera preferably comprises the following components: an imaging sensor 83, a lens mount 84, an output cable connector housing 85, and an output cable connector 86. The sensor 83 is preferably able to run in two modes of operation: video mode and camera mode. In video mode, the operator manipulates the device much like a regular video camera for positioning and manual focus. In this mode, a low resolution, high frame rate image stream is produced. In camera mode, the present invention will temporarily change the imaging sensor settings so that the highest possible image resolution is preferably achieved, at the expense of a lower frame rate. The final XP and PP images of the present invention are preferably acquired in camera mode, and are stored for later review, image annotation, and processing. XP and/or PP images can also be registered (aligned) and then faded into each other to aid a clinician in arriving at a diagnosis FIG. 7A shows a side view of a presently preferred embodiment of the detection system which contains two cameras, and FIG. 7B shows a side view of another embodiment of the detection system which contains only one camera. The placement of the front lens 34, polarizing element (such as a polarizing beam splitter) 22, and the cameras 20 and 24 are shown therein.

For a two camera system, as seen in FIG. 7A, the optics of the first camera 20 are preferably designed to capture a full field of view of the subject, and the secondary optics of the second camera 24 are preferably designed to capture a magnified view of a smaller region-of-interest (typically being able to resolve the smallest diagnostically relevant feature). In the preferred embodiment which uses two sets of LEDs, the optical paths of the two sets of LEDs are polarized perpendicular to one another after being split by the PBS 22, and depending on which set of LEDs is turned on, the image outputs received and displayed by both cameras will be either (i) a full-view XP image; (ii) a magnified region-of-interest view PP image; (iii) a full-view PP image; or (iv) a magnified region-of-interest XP image. The PP and XP images are substantially co-registered because of the rapid switching between (or switching on and off) of the illumination source (LEDs), and can be used in conjunction with each other for diagnostic purposes, for example, fading between them. In the embodiment which uses only one set of LEDs, the optics of the two camera systems 20 and 24 are preferably designed to capture the same field of view of the subject, this view being either the full-view or a magnified region-of-interest view. Here, the image outputs received and displayed will be either (i) a full-view (or magnified) XP image or (ii) a full-view (or magnified) PP image.

For a single (one) camera system, as seen in FIG. 7B, the optics of the camera 24 are preferably either a fixed focal length lens configured to capture the full field of view of the subject, or a zoom lens configured to capture the full field of view of the subject as well as a magnified view of the subject.

Figure 8A:
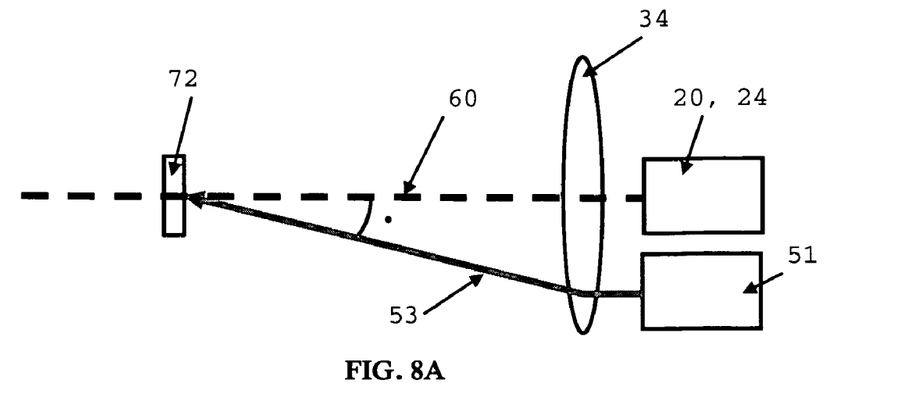
FIGS. 8A, 8B, and 8C are schematics of the focusing subsystem which show the camera object plane, the camera and the position of the focused light relative to the cervix, for three different focus states.
Figure 8B:
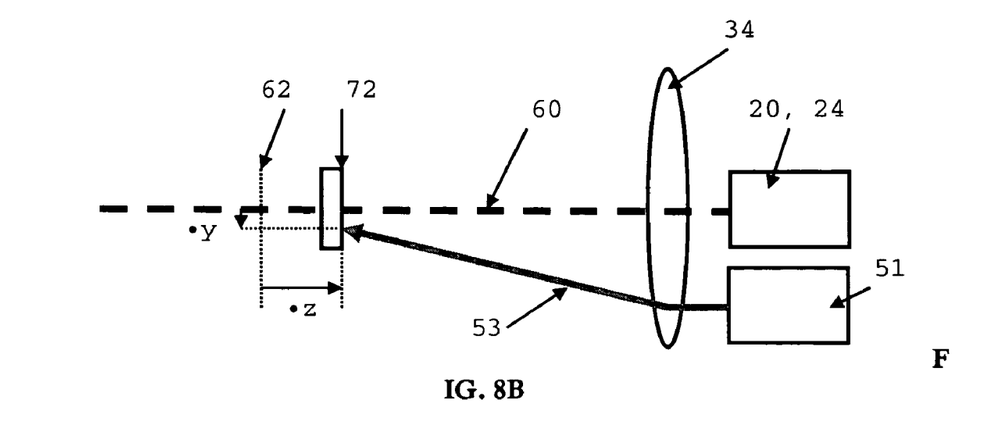
Figure 8C:
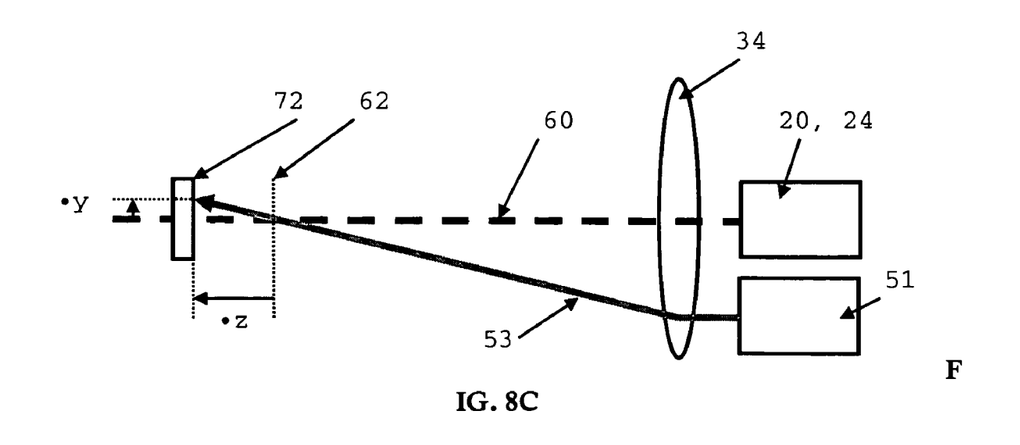

The presently preferred embodiment of the invention also includes a focusing subsystem which helps achieve optimal focus of the images. This focusing subsystem analyzes images taken in the video mode to assess if the invention is in focus before images are acquired in camera mode. As displayed in FIGS. 8A, 8B and 8C, a focus light source (e.g. a focused LED or a laser) 51 produces a focus beam 53 that is focused toward the optical axis 60 through a lens 34, the displacement of the focus beam ($\Delta y$) in the field of view of the camera uniquely determines the distance ($\Delta z$) needed to align the examined region (region or object of interest) 72 with the camera object plane 62, where the focus beam 53 meets the optical axis 60. When the examined region is aligned with the camera object plane, as seen in FIG. 8A, the examined region is 'in focus'. When the focus beam is in the lower pixels of the image, the examined region is too close, as shown in FIG. 8B, and the subsystem is 'out of focus'. When the focus beam is in the upper pixels of the image, the examined region is too far, as seen in FIG. 8C, and the subsystem is also 'out of focus'. The output of the focusing subsystem suggests which direction the operator should move the device to achieve optimal focus. Although the focus light source 51 is shown to be located below the optical axis 60 in FIG. 8A, FIG. 8B and FIG. 8C, it can be positioned anywhere off the optical axis. The system is operable as long as the focus beam and the optical axis are within a certain angle ($\square$) of each other, and the focus beam is not obstructed by any object other than the region of interest. The focus system is operable when the angle $\alpha$ is approximately between the ranges of 2 to 60 degrees. Preferably the angle $\alpha$ should be approximately in the range of 4 to 15 degrees. Optimally, the angle should be approximately in the range of 5 to 8 degrees.

Figure 9:
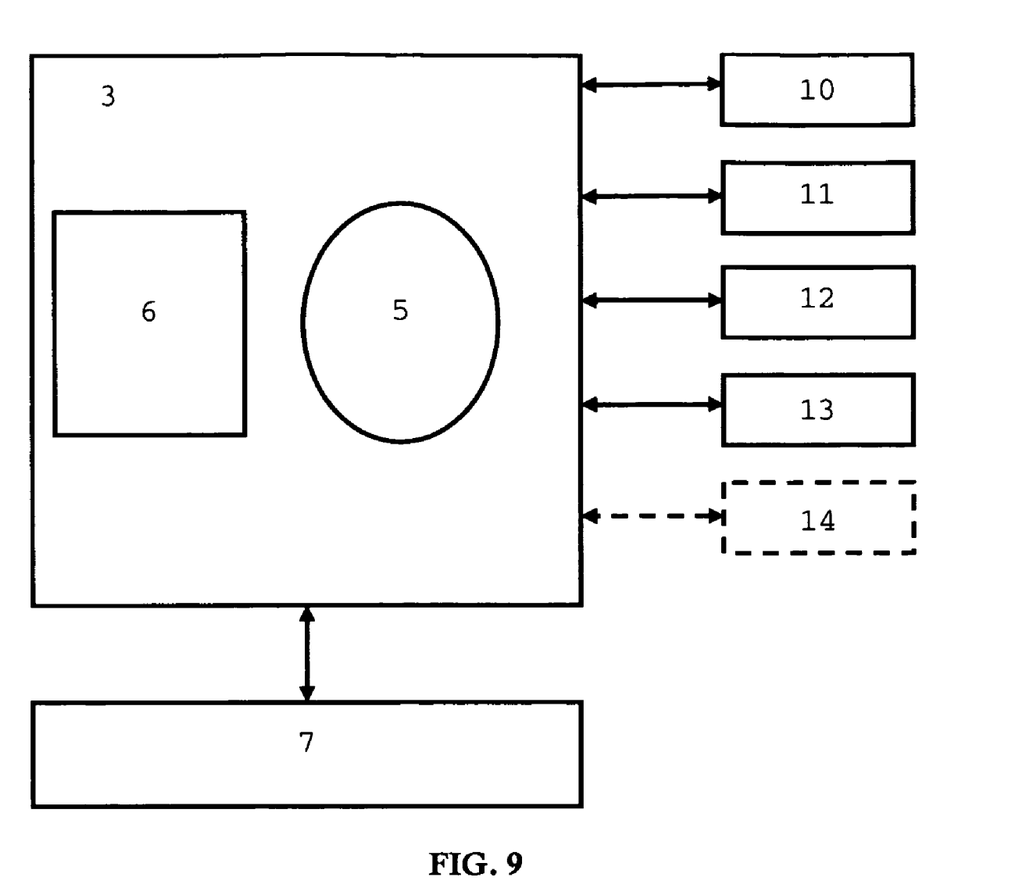
FIG. 9 is a flow chart of the data management system.

The presently preferred embodiment of the invention also includes a data management system. FIG. 9 shows a flowchart of the data management system. The data management system 3, includes a database of image and patient data, and interacts with the data acquisition system 7 and external sources, such as PACS (Picture Archiving and Communication System) 10, pathology reports 11, patient data records 12, telemedicine applications 13, and optional other sources defined by the user 14. PACS refer to computers or networks dedicated to the storage, retrieval, distribution and presentation of images. The medical images are preferably stored in a format that is independent of this invention and widely used. The most common format for medical image storage is presently DICOM (Digital Imaging and Communications in Medicine).

This data management system allows for a completely digital data flow, simplifying data transfer and storage, and minimizing the risk of human error. The data management system allows for (i) the use of image-enhancement algorithms; (ii) the use of image-processing algorithms; (iii) the use of annotation programs; (iv) digital archiving; and (v) remote viewing. This also allows the invention to (i) perform system diagnostics; (ii) present more comprehensive system information to the operator and technicians; and (iii) include comprehensive information, with respect to each image data set, about the state of the system when the images were acquired. It also preferably contains a fully integrated user interface, in which physical buttons are tied to the hardware and software platforms, permitting the functionality of the device to adapt, if necessary, to new functions.

INDUSTRIAL APPLICABILITY

This invention uses LEDs and cross-polarization to produce bright, high-resolution digital images, both with and without glint, that preserves image clarity while suppressing glint, and creates both cross-polarized images (glint-free images) and parallel-polarized images (images with glint), preferably at multiple magnifications. The invention is applicable to any imaging device in which it is desirable to enhance visualization of a subject (such as tissue or an organ) in a field of view by using at least one image with glint and a glint-free image.

What is claimed is:
1. A device for enhancing visualization of tissue in a field of view comprising:
   a first set of LEDs to emit light onto said field of view, whereby when said first set of LEDs is turned on, said first set of LEDs emits light onto said field of view through a first illumination polarizer placed between said first set of LEDs and said field of view, to create polarized light in said field of view having a first polarization orientation, and wherein said polarized light having said first polarization orientation is reflected by said tissue as first total reflected light;
   a second set of LEDs to emit light onto said field of view, whereby when said second set of LEDs is turned on, said second set of LEDs emits light onto said field of view through a second illumination polarizer placed between said second set of LEDs and said field of view, to create polarized light in said field of view having a second polarization orientation, and wherein said polarized light having said second polarization orientation is reflected by said tissue as second total reflected light;
   wherein said first set of LEDs and said second set of LEDs all emit visible light of the same color;

wherein said second polarization orientation is substantially perpendicular to said first polarization orientation;

a polarizing element to receive said first total reflected light and said second total reflected light and split said total reflected light into a first parallel-polarized output and a first cross-polarized output when said first set of LEDs is illuminated, and a second parallel-polarized output and a second cross-polarized output when said second set of LEDs is illuminated;

a first camera to receive said first parallel-polarized output to create a first parallel-polarized image when said first set of LEDs is illuminated, and to receive said second cross-polarized output to create a second cross-polarized image when said second set of LEDs is illuminated;

a second camera to receive said first cross-polarized output to create a first cross-polarized image when said first set of LEDs is illuminated, and to receive said second parallel-polarized output to create a second parallel-polarized image when said second set of LEDs is illuminated;

electronic switching means to rapidly switch between illuminating said first set of LEDs and illuminating said second set of LEDs to reduce influence from patient movement between successive images, allowing for better registration between said successive images; and whereby said parallel-polarized images and said cross-polarized images enhance visualization of said tissue.

2. A device for enhancing visualization of tissue in a field of view comprising:

a first set of LEDs to emit light onto said field of view, whereby when said first set of LEDs is turned on, said first set of LEDs emits light onto said field of view through a first illumination polarizer placed between said first set of LEDs and said field of view, to create polarized light in said field of view having a first polarization orientation, and wherein said polarized light having said first polarization orientation is reflected by said tissue as first total reflected light;

a second set of LEDs to emit light onto said field of view, whereby when said second set of LEDs is turned on, said second set of LEDs emits light onto said field of view through a second illumination polarizer placed between said second set of LEDs and said field of view, to create polarized light in said field of view having a second polarization orientation, and wherein said polarized light having said second polarization orientation is reflected by said tissue as second total reflected light;

wherein said second polarization orientation is substantially perpendicular to said first polarization orientation;

a polarizing element to receive said first total reflected light and said second total reflected light and split said total reflected light into a first parallel-polarized output and a first cross-polarized output when said first set of LEDs is illuminated, and a second parallel-polarized output and a second cross-polarized output when said second set of LEDs is illuminated;

a camera to receive one of said cross-polarized outputs to create a cross-polarized image when one of said set of LEDs is illuminated, and to receive one of said parallel-polarized outputs to create a parallel-polarized image when the other set of LEDs is illuminated;

electronic switching means to rapidly switch between illuminating said first set of LEDs and illuminating said second set of LEDs to reduce influence from patient movement between successive images, allowing for better registration between said successive images; and whereby said cross-polarized image and said parallel-polarized image enhance visualization of said tissue.

3. A device for enhancing visualization of tissue in a field of view comprising:

a first set of LEDs to emit light onto said field of view, wherein all LEDs in said first set of LEDs emit visible light of the same color;

an illumination polarizer placed between said first set of LEDs and said field of view to cause said light emitted onto said field of view; to become horizontally-polarized light, wherein said horizontally-polarized light is reflected by said tissue as total reflected light;

a polarizing element to receive said total reflected light that both polarizes and splits said total reflected light into first and second beams of light which contain substantially perpendicular polarization orientations to one another, wherein one of said polarization orientations is substantially parallel to polarization of said horizontally-polarized light and the other of said polarization orientations is substantially perpendicular to polarization of said horizontally-polarized light, whereby said polarizing element receives said total reflected light and splits said total reflected light into a parallel-polarized output and a cross-polarized output;

a first camera to receive said cross-polarized output to create a cross-polarized image;

a second camera to receive said parallel-polarized output to create a parallel-polarized image; and whereby said cross-polarized image and said parallel-polarized image enhance visualization of said tissue.

4. A device according to any one of claim 1 or 2, wherein said first illumination polarizer and said second illumination polarizer are preferably integrally formed.

5. A device according to any one of claim 1 or 3, wherein said first camera is at a first magnification and said second camera is at a second magnification, wherein said second magnification is greater than said first magnification.

6. A device according to any one of claim 1, 2, or 3, further comprising a focusing subsystem to achieve optimal focus.

7. A device according to any one of claim 1, 2, or 3, further comprising a computerized data management system for archival purposes and for the annotation of digital data.

8. A process to suppress glint and preserve image clarity comprising:

polarizing unpolarized light from LEDs to produce polarized light having a first polarization orientation;

illuminating a field of view containing tissue with said polarized light having a first polarization orientation;

reflecting said polarized light off said tissue as total reflected light;

polarizing and splitting said total reflected light into a parallel-polarized output and a cross-polarized output;

rapidly electronically switching between said parallel-polarized output and said cross-polarized output to reduce influence from patient movement between successive images, allowing for better registration between successive images;

collecting said rapidly electronically switched parallel-polarized outputs and said cross-polarized outputs;

producing a set of cross-polarized images from said cross-polarized output and a set of parallel-polarized images from said parallel polarized outputs; and whereby said set of cross-polarized image and said set of parallel-polarized images can be registered and faded into each other to enhance visualization of said tissue.

9. A process to suppress glint and preserve image clarity comprising:

polarizing unpolarized light from LEDs to produce polarized light having a first polarization orientation;

illuminating a field of view containing tissue with said polarized light having a first polarization orientation;

reflecting said polarized light off said tissue as total reflected light;

polarizing and splitting said total reflected light into a parallel-polarized output and a cross-polarized output;

rapidly electronically switching between said parallel-polarized output and said cross-polarized output to reduce influence from patient movement between successive images, allowing for better registration between successive images;

collecting said rapidly electronically switched cross-polarized outputs;

producing a set of cross-polarized images from said cross-polarized outputs; and whereby said set of cross-polarized images enhances visualization of said tissue by removing glint to allow for deeper layers of said tissue to be visualized at multiple magnifications.

* * * * *